United States Patent [19]

Murphree et al.

[11] Patent Number: 5,536,873
[45] Date of Patent: Jul. 16, 1996

[54] PREPARATION OF PENTENOIC ACID

[75] Inventors: Bruce Murphree, Beaumont, Tex.; Ronnie Ozer, Newark, Del.

[73] Assignees: E. I. du Pont de Nemours and Company, Wilmington, Del.; DSM N.V., Galeen, Netherlands

[21] Appl. No.: 354,842

[22] Filed: Dec. 9, 1994

[51] Int. Cl.$^6$ .......................... C07C 69/52; C07C 57/02
[52] U.S. Cl. ............................................ 560/205; 562/598
[58] Field of Search ............................... 560/205; 562/598

[56] References Cited

U.S. PATENT DOCUMENTS 5,228,903  2/1994  Bunel et al. ........................... 502/598

*Primary Examiner*—Paul J. Killos

[57] ABSTRACT 3-pentenoic acid or the R ester of pentenoic acid is produced by treating pentenoyl chloride in a reactive distillation zone with ROH where R is hydrogen or hydrocarbon of 1 to 6 carbon atoms. Butadiene may be reacted with HCl that is formed by the hydrolysis of pentenoyl chloride, and the butadiene converted to chlorobutene, and the chlorobutene reacted with carbon monoxide to form pentenoyl chloride.

5 Claims, 1 Drawing Sheet

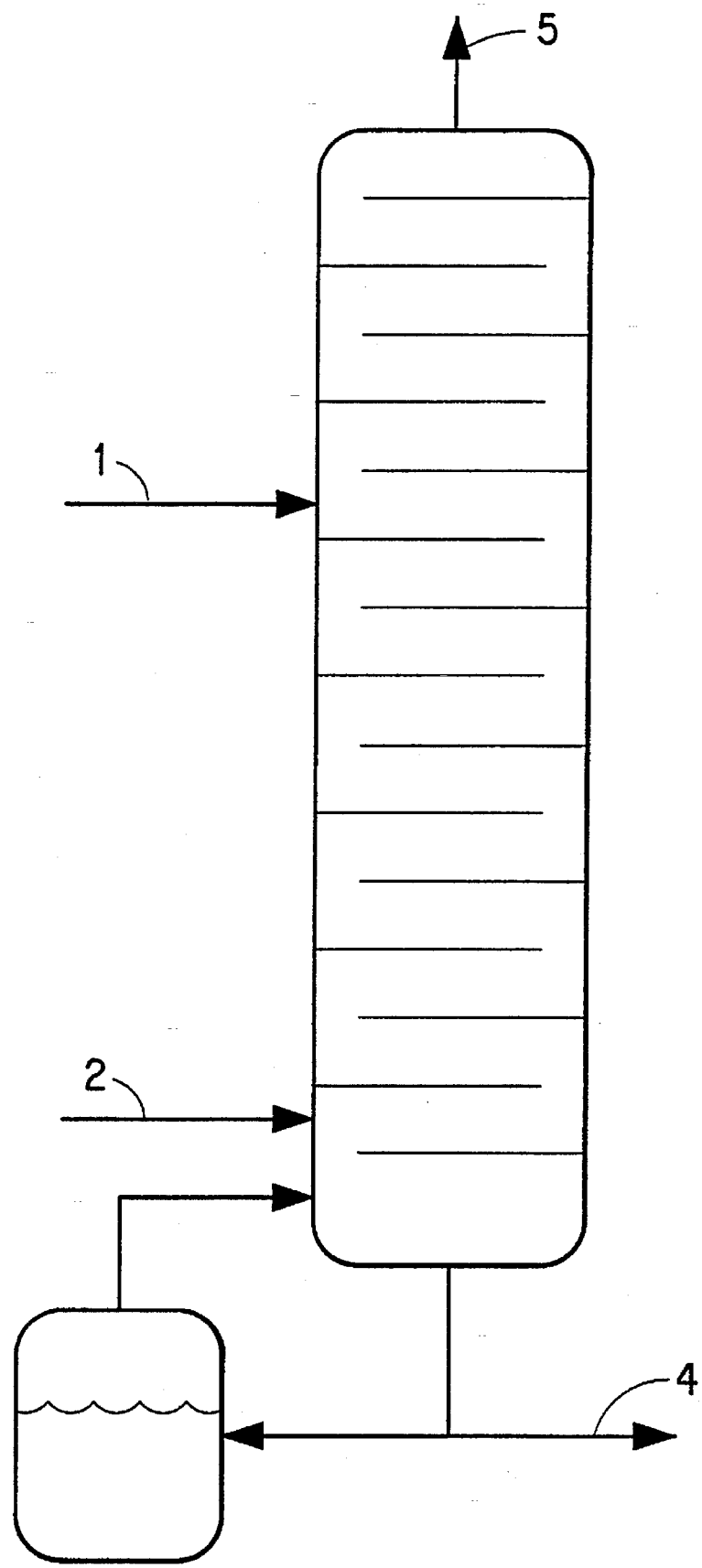

PREPARATION OF PENTENOIC ACID

FIELD OF THE INVENTION

This invention relates to the preparation of pentenoic acid or the R ester of pentenoic acid by the reaction of pentenoyl chloride with ROH in a reactive distillation zone.

BACKGROUND OF THE INVENTION

The preparation of 1-chloro-2-butene by the reaction of butadiene and hydrogen chloride is taught in U.S. Pat. No. 3,055,954 to Montagna et al.

The preparation of unsaturated carboxylic acid halides by the reaction of 1-chloro-2-butene (crotyl chloride) and carbon monoxide and a palladium catalyst is taught in U.S. Pat. No. 3,338,961 to Closson et al. See Example 8 in particular. Journal of the Chemical Society, 1964, pages 1588–1594, describes the use of palladium chloride complexes to react 3-chloro-1-butene with carbon monoxide to form 3-pentenoyl chloride. See Table 2, Page 1589.

The preparation of 3-pentenoic acid from pentenoyl chloride is disclosed in Bunel et al. U.S. Pat. No. 5,288,903.

The reaction of acyl halides with water to form acids is taught in standard organic chemistry textbooks.

3-pentenoic acid is an intermediate in the preparation of adipic acid from butadiene. See Burke U.S. Pat. No. 4,788,333. Adipic acid is a monomer used in the preparation of 6,6 nylon.

It is an object of the present invention to provide a process for the production of 3-pentenoic acid and 3-chloro-1-butene and 1-chloro-2-butene by a process in which there is less yield loss than when these desired products are formed in separate reactions.

SUMMARY OF THE INVENTION

The present invention is a process for the preparation of compounds having the formula

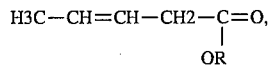
OR which comprises: (a) feeding pentenoyl chloride (which may be contained in a mixture with for example chlorobutene) to a reactive distillation zone maintained at a temperature above about 65 degrees C. and below about 125 degrees C., (b) feeding a compound of the formula ROH, where R is hydrogen or a hydrocarbon radical having 1 to 6 carbon atoms to the reactive distillation zone at a point below the feed point of the mixture of step (a), (c) removing HCl near the top of the reactive distillation zone, and (d) removing

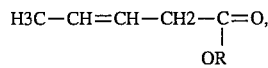
OR near the bottom of the reactive distillation zone. Preferably, butadiene is reacted with the HCl formed to form chlorobutene. The reaction of the HCl formed and the butadiene may take place by feeding the butadiene to a tray near the top of the reactive distillation zone, or the reaction may take place in a separate reactor. The chlorobutene may be used as a feed material for the carbonylation reaction and formation of pentenoyl chloride. Normally, the mixture containing pentenoyl chloride fed to the reactive distillation zone also contains chlorobutene. In the process for the conversion of pentenoyl chloride contained in a mixture with chlorobutenes to pentenoic acid only minor amounts of chlorovaleric acid are formed.

The invention is also a process for the conversion of pentenoyl chloride contained in a mixture with chlorobutenes to pentenoic acid with the formation of only minor amounts of chlorovaleric acids and valerolactone which comprises: (1) feeding said mixture to a reactive distillation zone maintained at a temperature above the boiling point of chlorobutenes but below the boiling point of pentenoyl chloride, (2) feeding water to the reactive distillation zone at a point below the feed point of said mixture, (3) removing chlorobutene and HCl near the top of the reactive distillation zone, and (4) removing pentenoic acid near the bottom of the reaction zone.

The invention is also a process for the conversion of pentenoyl chloride contained in a mixture with chlorobutenes to methyl 3-pentenoate with the formation of only minor amounts of methyl chloride and chloromethyl valerates which comprises: (1) feeding said mixture to a reactive distillation zone maintained at a temperature above the boiling point of chlorobutenes but below the boiling point of pentenoyl chloride, (2) feeding methanol to the reactive distillation zone at a point below the feed point of said mixture, (3) removing chlorobutene and HCl near the top of the reactive distillation zone, and (4) removing methyl 3-pentenoate near the bottom of the reaction zone.

BRIEF DESCRIPTION OF THE DRAWING

The drawing is a schematic cross sectional view of a reactive distillation column suitable for the hydrolysis of pentenoyl chloride in accordance with the invention.

DETAILED DESCRIPTION

The chlorobutene used in the preparation of 3-pentenoyl chloride may be a mixture of 3-chloro-1-butene and 1-chloro-2-butene, and may be produced by reacting butadiene and hydrogen chloride.

The reaction of chlorobutene with carbon monoxide to form 3-pentenoyl chloride may be carried out by means of a palladium catalyst. The palladium catalyst may be a mixture of palladium compounds. Suitable palladium compounds are disclosed in Bunel et al. U.S. Pat. No. 5,288,903.

After forming the reaction mixture containing 3-pentenoyl chloride and cholorbutenes, the carbon monoxide is separated from the reaction mixture. The carbon monoxide is stripped from the reaction mixture by heating the mixture at low pressure.

The 3-pentenoyl chloride and chlorobutenes are then separated from the reaction mixture by distillation preferably at a temperature in the range of about 50 to about 120 degrees C. and at a pressure in the range of about 0.1 to 2 atmospheres.

The mixture containing 3-pentenoyl chloride (or pure 3-pentenoyl chloride) is then fed to a reactive distillation zone such as a reactive distillation column shown in the Figure. The 3-pentenoyl chloride is fed at point 1, and ROH at point 2. The 3-pentenoyl chloride moves down the column, and the ROH compound moves up the column. The 3-pentenoyl chloride is hydrolyzed when R is hydrogen to 3-pentenoic acid, and an HCl formed. Chlorobutenes (if any) move up the column. The 3-pentenoic acid formed is removed from the bottom of the column at point 4. A mixture of containing HCl is taken off the top of the column at point 5. If desired, the HCl in this mixture may be reacted in another column (zone) with butadiene to form chlorobutene.

The process can be operated in the same manner using any other ROH compound, where R is hydrocarbon of 1 to 6 carbon atoms. If R is other than hydrogen the product will be the R ester of pentenoic acid. A preferred ROH compound is methanol.

Pentenoyl chloride is a valuable intermediate for the synthesis of pentenoic acid or ester which is needed to manufacture adipic acid. Hydrolysis of pentenoyl chloride in the presence of 75 weight % chlorobutenes is a mass transfer limited reaction requiring excess aqueous phase. It is desirable to hydrolyze with a minimum of water (near stoichiometric) to minimize chlorovaleric acid formation. In the methanol case it is desirable to minimize methanol to prevent methyl chloride formation. The reactive distillation concept keeps the hydrogen chloride separate from the product acid or methanol by boiling point, therefore, minimizing methyl chloride and chloro-valeric acids.

EXAMPLE 1

A mixture of 25% pentenoyl chloride and 75% chlorobutenes (by weight) was fed to tray 15 (from the bottom) of a 20 tray 1 inch Oldershaw distillation column. Water in 20% stoichiometric excess was fed to 100 ml pot. The chlorobutene was recovered overhead with some excess water in high purity. The hydrogen chloride was scrubbed from the off gas with water and recovered. The product 3-pentenoic acid from the tails showed 0.1% water and less than 0.04% chloro-valeric acids.

EXAMPLE 2

A 7 mm Teflon spinning band distillation column operating at 1500 rpm was used with syringe pumps feeding water to the pot and pentenoyl chloride to the top. Chlorobutene was not included in these first experiments to test the reaction of pentenoyl chloride separate from the chlorobutene stripping. The 50 ml pot was charged with 20 grams of 3-pentenoic acid and heated to 130 C. The spinning band was started and pentenoyl chloride was fed to the top of the column at 15.0 ml/hr and demineralized water to the pot at 2.2 ml/hr (stoichiometric ratio). The pot was maintained at 130 C. +/−5 C. for 60 minutes. The head temperature remained below 30 C. throughout. The vent gas was scrubbed continuously with water. Analysis of the scrubber showed 47% conversion of the pentenoyl chloride by chloride balance. Analysis of the pot contents showed a selectivity to 4-chlorovaleric acid from pentenoyl chloride of 0.6%. There was no production of valerolactone or 2-pentenoic acid in this run because of the low pot temperature which inhibits isomerization and chlorovaleric acid dehydrochlorination.

EXAMPLE 3

In the continuous reactive distillation of pentenoyl chloride and water 2 10 tray vacuum jacketed 1 inch Oldershaw columns were stacked with a feed point and thermocouple at the mid point (tray 10). 50.02 grams valeric acid was charged to the 100 ml pot as startup material and then heated to boiling (191 C. owing to the backpressure of two water scrubbers). When boilup in the column was sufficient to inventory the bottom ten trays with valeric acid, feed to the column was begun. Syringe pumps were used to feed 2.00 ml/min of a 75 wt % chlorobutene/25 wt % pentenoyl chloride mixture to tray 10, and 5.86 ml/hr (40% excess) of water to the base. Material was pumped from the base continuously at 0.42 ml/min with an LC pump to maintain a relatively constant level in the pot. The hold up time in the base was approximately 120 minutes. The temperature in the base rose over the 145 minutes of running to 200 C. as 3-penetenoic acid displaced the startup valeric acid. The power input to the base was adjusted during the run to maintain approximately 100 C. at the feed tray. The overhead temperature remained at 74 C. throughout the run. Analysis of the product streams showed less than 0.03 wt % impurities in the overhead chlorobutenes (excluding HCl and excess water which was carried overhead) and less than 0.5% chlorobutene loss in the tails. The pentenoyl chloride conversion was greater than 99.9% with selectivity to valerolactone and 2-pentenoic acid of 1.5% in the tails stream (steady state prediction of 4.5%). No chlorovaleric acid production was observed in this run (the high tails temperature causes dehydrochlorination of any of these compounds with adequate hold up time).

EXAMPLE 4

A 20 tray 1 inch vacuum jacketed Oldershaw was used with 3 feed points, and 6 tray thermocouples for temperature profile control. A mixture of 45.45 g 3-pentenoic acid and 5.0 g valeric acid was charged to the 100 ml pot and heated to boiling. A mixture of 50 wt % chlorobutenes/50 wt % pentenoyl chloride was fed to tray 15 at 4.0 ml/min from a syringe pump and water was fed at tray 0 (the base) at 21.2 ml/hr (20% excess) for 100 minutes (approximately 3 liquid turnovers at a hold up time of approximately 30 minutes in the base). The temperature profile was controlled by varying the distillate rate to maintain a tray 13 temperature of 100 C. The reflux ratio was therefore unknown. The overhead stream was two phase, an organic phase consisting of the feed chlorobutenes with 0.14% pentenoic acids, and a small aqueous phase of primarily concentrated aqueous HCl (from the excess water). The tails showed complete conversion of the pentenoyl chloride with a selectivity to 2-pentenoic acid and valerolactone of 1.76%. The yield of 3-pentenoic acid was 98.1%.

EXAMPLE 5

The apparatus in Example 4 was charged with 40.31 grams methylvalerate, 29.97 grams chlorobutene and taken to the methyl valerate boiling point (135 C.) with the chlorobutene inventorying the trays. Tray 10 was fed with a mixture of 25 wt % valeryl chloride/75 wt % chlorobutenes at 2.0 ml/min and methanol was fed to the base at 9.02 ml/hr (10% excess). The temperature profile was maintained with tray 5 at 100 C. throughout the 180 minute run. The distillate was two phase, a predominant chlorobutene phase with 0.5 wt % methyl valerate, and 1.2 wt % methanol and a phase of 45 wt % methanol, 20 wt % HCl, 24 wt % chlorobutenes and 8 wt % water. The valeryl chloride conversion was approximately 75%, with excess methanol going overhead in the distillate. HCl vapor was again scrubbed in water for recovery.

EXAMPLE 6

The apparatus in Example 4 was charged with 40.27 grams methyl valerate, 25.08 grams chlorobutenes and taken to the methyl valerate boiling point (135 C.) with the chlorobutene inventorying the trays. Tray 10 was fed with a mixture of 25 wt % pentenoyl chloride/75 wt % chlorobutenes at 3.0 ml/min and methanol was fed to the base at 13.7 ml/hr (10% excess). The temperature profile was maintained with tray 5 at 100 C. throughout the 130 minute run. The distillate was two phase; the predominant chlorobutene phase with 0.1 wt % methyl valerate, and 0.4 wt % methanol. The pentenoyl chloride conversion was approximately 68%, with excess methanol going overhead in the distillate. HCl vapor was again scrubbed in water for recovery. Methyl-2-pentenoate selectivity was low, 0.08%. The tails showed 0.8% chlorobutenes or 0.7% of the feed.

EXAMPLE 7

In the same apparatus used above, phenol was fed at substoichiometric amounts to tray 15 while 2.0 ml/min 50 wt % pentenoyl chloride/50 wt % chlorobutenes was fed to tray 10, with an initial startup material of 15.5 grams methyl valerate and 15.01 grams chlorobutenes already boiling in the column. The boiling point of the pot rose during the run as phenyl pentenoate was formed. No phenol was seen in the tails or overhead indicating complete conversion, with phenyl pentenoate reaching 38 wt % in the tails. HCl vapor was scrubbed from the vent as before. The overhead chlorobutene showed no traces of phenol or phenyl pentenoate or a second phase.

What is claimed is

1. A process for the preparation of pentenoic compound having the formula

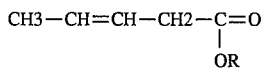

which comprises: (a) feeding pentenoyl chloride to a reactive distillation zone maintained at a temperature above about 65 degrees C. and below about 125 degrees C., (b) feeding a compound of the formula ROH, where R is hydrogen or a hydrocarbon radical having 1 to 6 carbon atoms to the reactive distillation zone at a point below the feed point of the pentenoyl chloride (c) removing HCl near the top of the reactive distillation zone, and (d) removing

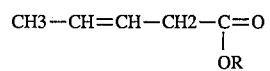

near the bottom of the reactive distillation zone.

2. The process of claim 1 in which butadiene is reacted with HCl formed to form chlorobutene and in which the chlorobutene is used as a feed material for the carbonylation reaction and formation of pentenoyl chloride.

3. The process of claim 1 in which the pentenoyl chloride fed to the reactive distillation zone also contains chlorobutene.

4. A process for the conversion of pentenoyl chloride contained in a mixture with chlorobutenes to pentenoic acid with the formation of only minor amounts of chlorovaleric acids and valerolactone which comprises: (1) feeding said mixture to a reactive distillation zone maintained at a temperature above the boiling point of chlorobutenes but below the boiling point of pentenoyl chloride, (2) feeding water to the reactive distillation zone at a point below the feed point of said mixture, (3) removing chlorobutene and HCl near the top of the reactive distillation zone, and (4) removing pentenoic acid near the bottom of the reaction zone.

5. A process for the conversion of pentenoyl chloride contained in a mixture with chlorobutenes to methyl 3-pentenoate with the formation of only minor amounts of methyl chloride and chloromethyl valerates which comprises: (1) feeding said mixture to a reactive distillation zone maintained at a temperature above the boiling point of chlorobutenes but below the boiling point of pentenoyl chloride, (2) feeding methanol to the reactive distillation zone at a point below the feed point of said mixture, (3) removing chlorobutene and HCl near the top of the reactive distillation zone, and (4) removing methyl 3-pentenoate near the bottom of the reaction zone.

* * * * *